United States Patent [19]

Illum

[11] Patent Number: 5,707,644
[45] Date of Patent: Jan. 13, 1998

[54] SMALL PARTICLE COMPOSITIONS FOR INTRANASAL DRUG DELIVERY

[75] Inventor: Lisbeth Illum, The Park, England

[73] Assignee: Danbiosyst UK Limited, Nottingham, England

[21] Appl. No.: 359,937

[22] Filed: Dec. 20, 1994

Related U.S. Application Data

[63] Continuation of Ser. No. 65,676, May 21, 1993, abandoned, which is a continuation-in-part of Ser. No. 842,351, filed as PCT/GB90/01678, Nov. 1, 1990, abandoned.

[30] Foreign Application Priority Data

Nov. 4, 1989 [GB] United Kingdom ............ 8924935

[51] Int. Cl.$^6$ ...................................... A61K 9/16
[52] U.S. Cl. .................... 424/434; 424/489; 424/499; 424/500; 424/501; 514/866
[58] Field of Search ............................ 424/434, 489, 424/493, 499, 500, 501; 514/866

[56] References Cited

U.S. PATENT DOCUMENTS

| | | | |
|---|---|---|---|
| 4,294,829 | 10/1981 | Suzuki et al. | 424/241 |
| 4,847,091 | 7/1989 | Illum | 424/455 |
| 5,204,108 | 4/1993 | Illum | 424/434 |

FOREIGN PATENT DOCUMENTS

| | | |
|---|---|---|
| 0122036 | 10/1984 | European Pat. Off. |
| 88/09163 | 12/1988 | WIPO |

OTHER PUBLICATIONS

Illum, Nato ASI Symposium pp. 205–210 (1986).
Salzman et al New Engl. J. Med. 312, 1078 (1985).
Hansen, Advanced Delivery System for Peptide & Proteins p. 233 (1988).
Davis ACM Symp. Ch. 15. p. 201 (1987).
Lisbeth Illum, "Drug Delivery For Nasal Application," *Arch Pharm. Chem.*, 94:127–135 (1986).
Miromoto et al., "Enhancement of nasal absorption of insulin and calcitonin using polyacrylic acid gel," *J. Pharm. Pharmacol.* 37:134 (1985).
Russell, "Starch Microspheres as Drug Delivery Systems," *Pharm. International*, 260–262 (1983).

*Primary Examiner*—Gollamudi S. Kishore
*Attorney, Agent, or Firm*—Arnall Golden & Gregory, LLP

[57] ABSTRACT

A drug delivery composition for intranasal delivery comprises a plurality of bioadhesive microspheres and active drug associated with each microsphere, at least 90 wt % of the microspheres having a diameter in the range 0.1 μm to 10 μm. The microspheres may be of starch, gelatin, dextran, collagen or albumin. Suitable drugs include peptides, such as insulin, and antigenic vaccine ingredients. The composition may additionally comprise an absorption enhancer. The microspheres are administered in the nasal cavity by a means such that the product of the square of the microsphere diameter and the flow rate is greater than 2000 $\mu m^2$.liters/min.

13 Claims, 3 Drawing Sheets

SMALL PARTICLE COMPOSITIONS FOR INTRANASAL DRUG DELIVERY

CROSS-REFERENCE TO RELATED APPLICATION

This is a continuation of application Ser. No. 08/065,676 filed on May 21, 1993, now abandoned, which is a continuation-in-part of U.S. patent application Ser. No. 07/842,351 filed Mar. 24, 1992, abandoned, and continuation-in-part of PCT/GB90/01676 filed on Nov. 1, 1990, the teachings in this application being herein incorporated by reference.

The present invention relates to drug compositions and more particularly to a small particle drug composition which provides for the uptake of active drug across the nasal mucosa.

There is a need to provide effective absorption of high molecular weight material such as proteins and peptides across biological membranes. Normally such molecules are not taken up by the body if administered to the gastrointestinal tract, the buccal mucosa, the rectal mucosa or the vaginal mucosa or if given as an intranasal system. Because peptide hormones such as insulin and calcitonin have a high molecular weight and are readily decomposed by proteolytic enzymes such as pepsin, aminopeptidases, trypsin and chymotrypsin, not enough is absorbed to display an effective pharmacological effect and accordingly they have been administered by parenteral injection.

However, since the administration by injection causes pain, various attempts have been made to develop alternative methods of administration.

Recent studies with insulin have demonstrated that the absorption of such a compound can be increased if it is given together with a so-called absorption enhancer, such as non-ionic surfactants and various bile salt derivatives. An increased permeability of membranes in the presence of these types of surfactant material is not unexpected, indeed the literature in the field of gastroenterology contains a wide range of such absorption promoters. (For a review see Davis et al (editors), Delivery Systems for Peptide Drugs, Plenum Press, New York 1987.) However, such materials will probably not be acceptable for the chronic administration of pharmacological agents because of their irritant effects on membranes. This includes not only the non-ionic variety of surface active agents but also bile salts and bile salt derivatives (e.g. fusidic acid).

At the present time the nose is being proposed as an alternative route for the delivery of drugs that will act within the systemic circulation. Particular attention is being focused on nature-identical peptides or proteins, or analogues or fragments thereof, produced by recombinant DNA techniques. Other drugs that are being suggested are those that are poorly absorbed orally or are extensively metabolised either in the gastro-intestinal tract itself or are subject to first pass metabolism in the liver. However, most polypeptide drugs show a low bio-availability when administered intranasally.

The rapid clearance of nasal sprays from the nose can probably be considered to be a major factor in influencing loss of drugs from potential absorption surfaces. In addition, in the case of peptides and proteins, enzymatic degradation of the drug and molecular size may also have a role in giving low bioavailabilities.

Our earlier co-pending application WO88/09163 discloses intra-nasal microsphere formulations containing an enhancer and our earlier co-pending application WO89/0327 discloses intra-nasal microsphere formulations containing drugs of molecular weight below 6000 which do not require an enhancer. In both of these applications, the diameter of the microspheres is in the range 10 μm to 100 μm. EP 122 036 (Teijin Ltd.) discloses powdery formulations for nasal administration in which at least 90 wt % of the particles have an effective diameter ranging from 10 μm to 250 μm.

It is taught in the art that particles for nasal delivery should be of diameter greater than 10 μm. EP 122 036 states that in compositions in which more than 10 wt % of the particles are below 10 μm, more particles will go further into the lungs or escape from the nostrils. It is known to use particles of diameter less than 10 μm for delivery of drugs to the lungs. GB 1 381 872 and GB 1 520 248 (Fisons) describe powdery compositions of particles less than 10 μm which are administered by oral inhalation to the lungs.

It has now been found, surprisingly, that bio-adhesive microspheres of diameter less than 10 μm can be used effectively and advantageously to deliver drugs to the nasal mucosa.

A first aspect of the invention therefore provides a drug delivery composition for intranasal delivery comprising a plurality of bioadhesive microspheres and a systemically active drug, at least 90 wt % of the microspheres having a diameter of 0.1 μm or more but less than 10 μm. The drug can be contained in the microspheres, admixed with the microspheres or absorbed onto the microspheres. The term "bioadhesive" as used herein is defined as a substance which adheres to the nasal mucosa, preferably to a greater extent than microcrystalline cellulose. It is thought that such bio-adhesive microspheres interact with the glycoproteins in the mucus and/or the epithelial cells. The term "drug" is used to embrace any pharmacologically active agent, including hormones, polypeptides and vaccines or components thereof, for example isolated antigens or antigenic parts or mimics thereof.

For any particulate system consisting of a distribution of particle sizes, it is important to define exactly the way in which the diameter is measured. A powder system produced by milling or emulsification followed by suitable processing to yield microspheres (this includes both powders and bioadhesive microspheres) is expected to follow a so-called log normal distribution. Particle size measured by microscopic observation will give a number average distribution. This can be converted to a weight distribution (number-weight, mean diameter), using equations found in standard text books such as T. Allen, Particle Size Measurement second edition, Chapman and Hall, 1974 and Caserett, L. J. in Toxicology, edited by Casarett, L. J. and Doull, J., Macmillan, New York, 1975, chapter 9.

In the latter, it is stated that the customary expression of particle size is in terms of the median size, either count or mass. For a log normally distributed powder, conversion between a count median diameter (CMD) and a mass median diameter MMD is easily accomplished by a simple calculation where $\delta g$ is the geometric standard deviation:

$$\log M \text{ (Count)} = \log M' \text{(Mass)} - 6.9 \log^2 \delta g$$

The weight distribution can be measured directly by screening or sieving or by sedimentation balance. Details are given in the book by Allen (see above).

For a spherical particle, size is uniquely defined and it is possible to talk about a mean diameter. However, with non-spherical particles it is necessary to consider an effective diameter as the size of a sphere that corresponds to the particle under the chosen conditions of measurement. The various options are discussed in the book by T. Allen, where derived diameters are determined by measuring a size dependent property of the particle and relating it to a linear dimension. Effective diameter has been defined by Teijin, so far as it applies to their nasal delivery system, in EP 23359. They refer to a diameter as determined by the opening sizes of sieves. For example, a powder having an effective particle diameter (d) of $37<d\leq 44$ passes through a sieve having an opening size of 44 microns but does not pass through a sieve having an opening size of 37 microns.

A vibratory sieve may be used when the effective particle diameter of a powder is more than 37 microns, and a sonic sieve (Micro Hand Sifter SWM-2, a product of Tsutsui Rikagaku Kikai Co. Ltd.) may be used when the effective particle diameter of a powder is not more than 37 microns. It is believed that this definition also applies to EP 122 036 (Teijin Ltd.).

Thus, 90 wt % by weight of spherical microspheres of the present invention have a true mean weight diameter of less than the 10 μm effective diameter of the Teijin particles. Preferably 90 wt % of the microspheres are over 0.5 μm in diameter, more preferably over 1.0 μm and most preferably over 2 μm in diameter. Suitably, 95 wt % or 99 wt % of the particles satisfy one or more of these criteria.

Preferably the microspheres are prepared from a biocompatible material that will gel in contact with the mucosal surface. Substantially uniform solid microspheres are preferred. Starch microspheres (cross-linked if necessary) are a preferred material. Other materials that can be used to form microspheres include starch derivatives, modified starches such as amylodextrin, gelatin, albumin, collagen, dextran and dextran derivatives, polyvinyl alcohol, polylactide-co-glycolide, hyaluronic acid and derivatives thereof such as benzyl and ethyl esters, gellan gum and derivatives thereof such as benzyl and ethyl esters and pectin and derivatives thereof such as benzyl and ethyl esters. By the term "derivatives" we particularly mean esters and ethers of the parent compound that can be unfunctionalised or functionalised to contain, for example, ionic groupings.

Suitable starch derivatives include hydroxyethyl starch, hydroxypropyl starch, carboxymethyl starch, cationic starch, acetylated starch, phosphorylated starch, succinate derivatives or starch and grafted starches. Such starch derivatives are well know and described in the art (for example Modified Starches: Properties and Uses, O. B. Wurzburg, CRC Press Boca Raton (1986)). Suitable dextran derivatives include diethylaminoethyl-dextran (DEAE-dextran), dextran sulphate, dextran methyl-benzylamide dextran), dextran methyl-benzylamide carboxylates, carboxymethyl dextran, diphosphonate dextran, dextran hydrazide, palmitoyldextran and dextran phosphate.

Preparation of these microspheres is well described in the pharmaceutical literature (see for example Davis "Microspheres and Drug Therapy", Elsevier Biomedical Press, 1984, which is incorporated herein by reference). Emulsion and phase separation methods are both suitable. For example, albumin microspheres may be made using the water-in-oil emulsification method where a dispersion of albumin is produced in a suitable oil by homogenization techniques or stirring techniques, with the addition if necessary of small amounts of an appropriate surface active agent.

The size of the microspheres produced is a function of the speed of stirring or homogenization conditions used with the selected mixture of ingredients. By using a stirring speed or homogenization within the range 100–10000 rpm, microspheres within the desired size range of 0.1 μm to 10 μm will be produced. It is within the scope of the person skilled in the art to select the exact conditions for the desired microsphere size. The agitation can be provided by a simple laboratory stirrer or by more sophisticated devices such as a microfluidizer or homogenizer. The microspheres obtained may be sieved if necessary in order to remove the occasional over- or under-sized microsphere. This may also be done using other size separation techniques, such as air elutriation.

Emulsification techniques are also used to produce starch microspheres as described in GB 1 518 121 and EP 223 303 as well as for the preparation of microspheres of gelatin. Proteinaceous microspheres may also be prepared by coacervation methods such as simple or complex coacervation or by phase separation techniques using an appropriate solvent or electrolyte solution. Full details of the methods of preparing these systems can be obtained from standard text books (see for example Florence and Attwood, Physicochemical Principles of Pharmacy 2nd Ed., MacMillan Press, 1988, Chapter 8).

The following examples demonstrate preparation of microspheres within the desired size range of 0.1 μm to 10 μm.

Preparation of hyaluronic acid ester microspheres by solvent extraction

An emulsion was formed by mixing a 6% w/v solution of the polymer eg benzyl hyaluronic acid ester (Hyaff- 11) in dimethylsulphoxide with white mineral oil containing 0.5% Arlacel A. The inner phase was added to the outer oil phase (their respective ratio is 1:16 v/v) with continuous stirring for 10 minutes (1000 rpm). Ethyl acetate, the extraction solvent was then added to the emulsion at a ratio of 2:1 v/v. The extraction proceeds for 15 minutes at a stirring rate of 700 rpm until the microparticles are formed. The microsphere suspension was filtered and extensively washed with n-hexane and dried. Drug can be incorporated into the microspheres by addition to the initial polymer solution. The obtained size of microspheres was 2–10 μm.

The preparation of small starch microspheres using emulsification

A 10% starch gel was prepared by heating (70° C.) 5 g of starch with 40 ml of water until a clear gel was formed. After cooling water was added to a volume of 50 ml. 20 ml of this starch gel was then added to 100 ml of soya oil BP containing antioxidant and 1% v/v Span 80 and homogenised at 7000 rpm for 3 minutes. This emulsion was then added to 100 ml hot (80° C.) soya oil BP (containing antioxidant) and stirred at 1500 rpm with a paddle stirrer while heated to 115° C. over 15 minutes. The emulsion was left stirring at 115° C. for 15 minutes and then rapidly cooled by packing in ice while stirring. 100 ml of acetone was added and the microspheres were centrifuged at 4500 rpm for 15 minutes. The pellet was resuspended in acetone and separated into the desired size fraction by filtering through an appropriate sieve, for example a 0.5 μm fluoropore filter. The microspheres were then allowed to air dry. The microspheres produced were <10 μm diameter.

Production of small albumin microspheres

Albumin microspheres were produced by a modification of the method described by Ratcliffe et at (1984) *J. Pharm. Pharmacol.* 36, 431–436, which is incorporated herein by reference. One ml of 5% human serum albumin or ovalbumin at pH 6.8 was added to 25 ml of olive oil or light mineral oil with or without 0.25 ml of Span 85. The mixture was stirred in a mix-cell for 10 min under turbulent flow conditions to form a w/o emulsion, using a mechanical stirrer (Heidolph) at 775 rpm (Tachometer DOT 1, Compact Instruments). Glutaraldehyde solution 25% (w/v) was added to 3.6% (v/v) of aqueous phase and the emulsion stirred for a further 30 min to denature and cross-link the albumin. The microspheres were collected by centrifugation at 2500 g for 20 min. The oil was then removed and the spheres washed with diethyl ether followed by ethanol. The microspheres were collected by decantation. The microspheres produced were in the size range 0.1–10 μm.

Production of small starch microspheres 5 g potato starch were dissolved in 95 ml of water at about 90° C. A second solution was prepared from 3 g of polyethylene glycol ($m_w=6000$) and 47 ml of water. This solution was heated to about 70° C., whereafter the warm starch solution was added while stirring, to form an emulsion. When the two-phase system had formed (with the starch solution as the inner phase) the mixture was allowed to cool to room temperature under continued stirring, whereupon the inner phase was converted to gel particles. The particles were filtered off at room temperature and stirred in 100 ml of ethanol, whereafter the particles were again filtered off and laid to dry in air. The yield was 90% and the microspheres produced were <10 μm diameter.

The final microspheres can be modified by chemical cross-linking or heat treatment if desired.

The preparation of small albumin microspheres using an emulsification technique and heat stabilisation The following non-limited example illustrates the use of heat stabilisation. This is particularly suitable for albumin microspheres but can be used with any other microspheres according to the invention.

100 ml Soya oil was mixed with 1 ml of a 10% albumin solution and homogenised at 6000 rpm. The emulsion was added to 200 ml soya oil at 50° C. and stirred at 1500 rpm. The emulsion was then heated to 120° C. and equilibrated for 20 minutes at this temperature. The microspheres were then cooled to room temperature and washed with petroleum ether. The microspheres were then centrifuged at 4500 rpm for 15 minutes and the collected pellet was washed with ethanol followed by acetone. The microspheres were then filtered and allowed to air dry. Microspheres of 1–10 μm were prepared.

The preparation of small abbumin microspheres using an emulsification technique and chemical crosslinking The following non-limiting example is presented as one example of a method of preparing a microsphere which is modified by cross-linking.

100 ml Soya oil was mixed with 1 ml of a 10% albumin solution and homogenised at 6000 rpm. The emulsion was added to 200 ml soya oil at 50° C. and stirred at 1500 rpm.

To crosslink the microspheres, 100 μl of a 25% Glutaraldehyde solution was added dropwise and the emulsion stirred at 1500 rpm for a further 30 minutes. The microspheres were harvested by added petroleum ether, centrifuging and washing with petroleum ether.

The microspheres were then centrifuged at 4500 rpm for 15 minutes and the collected pellet was washed with ethanol followed by acetone. The microspheres were then filtered and allowed to air dry. Microspheres of 1–10 μm were prepared.

Suitable cross-linking agents for use with starch microspheres include epichlorohydrin, terephthaloyl chloride and sodium trimetaphosphate. Suitable agents for use with albumin microspheres include aldehydes such as formaldehyde and glutaraldehyde, oxidised dextran ("dextranox") and 2,3-butanediose, the latter also being suitable for use with gelatin microspheres. Agents such as $N,N,N^1,N^1$-tetramethylethylenediamine can be used with dextran microspheres.

The active agent can be incorporated into the microspheres during their formulation or sorbed into-onto the system after preparation. The effectiveness of the system can be controlled by the physical nature of the microsphere matrix and, for example, the extent of cross linking.

As an added advantage the particles may have variable controlled release characteristics through modifications made to the microsphere system, for example by controlling the degree of cross-linking or by the incorporation of excipients that alter the diffusional properties of the administered drug. It has been found that by increasing the heat stabilisation time or the time of exposure to the cross-linking agent during microsphere preparation, the release of the drug from the microsphere is delayed.

The amount of drug that can be carried by the microspheres is termed the loading capacity, which is determined by the physico-chemical properties of the drug molecule and in particular its size and affinity for the particle matrix. Higher loading capacities are to be expected when the administered drug is incorporated into the microspheres during the actual process of microsphere manufacture. It is known that for many peptides and proteins the amount of drug substance to be administered for a resultant therapeutic effect will be of the order of a few micrograms or less.

Microcapsules of a similar size, which are bioadhesive and which have controlled release properties, may also provide similar benefit in terms of an increased and modified bio-availability of administered drugs. These microcapsules can be produced by a variety of methods. The surface of the capsule can be adhesive in its own fight or can be modified by coating methods familiar to those skilled in the art. These coating materials are preferably bioadhesive polymers such as polycarbophil, carbopol, DEAE-dextran or alginates. These microcapsules are deemed to be "microspheres" for the purposes of this specification and, again, are more than 0.1 μm in diameter but less than 10 μm.

Using the combination of microspheres and drug, it has been found that the bioadhesive microsphere systems have the ability to enhance greatly the bioavailability of drugs, especially polar drugs, when they are administered together.

This potentiation of effect is believed to be due to the greater retention of the delivery systems in the nasal cavity.

The microsphere composition can also afford protection of the drug against degradation by enzymes.

The drug delivery system of the invention may advantageously comprise an absorption enhancer. By "enhancer", we mean any material which acts to increase absorption across the mucosa. Such materials include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolised to a normal cell constituent that does not have any significant irritant effect.

Preferred enhancing materials lysophospholipids, for example lysophosphatidylcholine obtainable from egg or soy lecithin. Other lysophosphatidylcholines that have different acyl groups as well as lyso compounds produced from phosphatidylethanolamines and phosphatidic acid which have similar membrane modifying properties may be used. Acyl carnitines (e.g. palmitoyl-dl-carnitine-chloride) is an alternative. A suitable concentration is from 0.02 to 20% w/v.

Other enhancing agents that are appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316–321 (which is incorporated herein by reference). Also agents that modify the membrane fluidity and permeability are appropriate such as enamines (e.g. phenylalanine enamine of ethylacetoacetate), malonates (e.g. diethyleneoxymethylene malonate), salicylates, bile salts and analogues and fusidates. Suitable concentrations are up to 20% w/v.

The same concept of delivery of a drug incorporated into or onto a bioadhesive microsphere with an added pharmaceutical adjuvant applies to systems that contain active drug and mucolytic agent, peptidase inhibitors or non-drug polypeptide substrate singly or in combination. Suitably mucolytic agents are thiol-containing compounds such as N-acetylcysteine and derivatives thereof. Peptide inhibitors include actinonin, amastatin, bestatin, chloroacetyl-HOLeu-Ala-Gly-NH$_2$, diprotin A and B, ebelactone A and B, E-64, leupeptin, pepstatin A, phisphoramidon, H-Thr-(tBu)-Phe-Pro-OH, aprotinin, kallikrein, chymostatin, benzamidine, chymotrypsin and trypsin. Suitable concentrations are from 0.01 to 10% w/v. The person skilled in the art will readily be able to determine whether an enhancer should be included.

The microsphere composition may be used with drugs selected from the following non-exclusive list: insulin, calcitonins (for example porcine, human, salmon, chicken, or eel) and synthetic modifications thereof, enkephalins, LHRH and analogues (Nafarelin, Buserelin, Zolidex), GHRH (growth hormone releasing hormone), nifedipin, THF(thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystildnine), DDVAP, Interferons, growth hormone (solatotropin) polypeptides or their derivatives (preferably with a molecular weight from 1000 to 300000), secretin, bradykinin antagonists, GRF (Growth releasing factor), THF, TRH (Thyrotropin releasing hormone), ACTH analogues, IGF (Insuline like growth factors), CGRP (Calcitorin gene related peptide) Atrial Natriuretic peptide, Vasopressin and analogues (DDAVP, Lypressin), Metoclopramide, Migraine treatment (Dihydroergotamine, Ergometrine, Ergotamine, Pizotizin), Nasal Vaccines (Particularly AIDS vaccines) FACTOR VIII, Colony Stimulating factors, G-CSF (granulocyte-colony stimulating factor), EPO Erythropoitin) PTH (Parathyroid hormone).

Further drugs include: antibiotics and antimicrobial agents such as tetracyline hydrochloride, leucomycin, penicillin, penicillin derivatives, erythromycin, gentamicin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, active vitamin D and vitamin C; sex hormones; hypotensives; sedatives; anti-tumour agents; steroidal anti-inflammatory agents such as hydrocortisone, prednisone, fluticasone, prednisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, medanamic acid, ibuprofen, diclofenac sodium, indomethacine, colchicine, and probenocid; enzymatic anti-inflammatory agents such as chymotrypsin and bromelain seratiopeptidase; anti-histaminic agents such as diphenhydramine hydrochloride, chlorpheniramine maleate and clemastine; anti-allergic agents and antitussive-expectorant antasthmatic agents such as sodium chromoglycate, codeine phosphate, and isoproterenol hydrochloride.

The molecular weight of the drug is preferably in the range 100 to 300,000.

In order to improve the properties, appearance or odour of the pharmaceutical composition, it may, if desired, contain any of known additives such as colouring agents, preservatives, antiseptics, etc. Examples of colouring agents include β-carotene, Red No. 2 and Blue No. 1; examples of preservatives include stearic acid, ascorbyl stearate and ascorbic acid; examples of antiseptics include p-hydroxybenzoate, phenol, chlorobutanol, benzylkonium chloride etc.; and examples of corrigents include menthol and citrus perfume.

A further embodiment of the invention provides a system for intranasal drug delivery comprising a drug delivery composition and container having an orifice through which the composition can be delivered to the nasal mucosa in a gas stream. The gas stream may be air or any other physiologically harmless gas. Preferably the means is such that, in use, the product of the flow rate and the square of the microsphere diameter is greater than 2000 μm$^2$ liters/min.

The means to deliver the microspheres, which are for example in a freeze dried form, to the nasal cavity is conveniently a nasal insufflator device or pressurised aerosol cannister. Examples of these are already employed for commercial powder systems intended for nasal application. The microspheres should be administered in a dry, air-dispensable form.

The insufflator produces a finely divided cloud of the dry powder or microspheres. The insufflator is preferably provided with means to ensure administration of a substantially fixed amount of the composition. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The in sufflator preferably has means such as a needle to break open the capsule or other device to provide holes through which jets of the powdery composition can be delivered to the nasal cavity.

The deposition in the nose will depend on two factors: the size of the particles (aerodynamic diameter) and flow rate (F) of inspiratory air.

The controlling factor is $(d_a)\,F$ where da is measured in microns and F in liters/min.

The product $(d_a)^2 F$ should exceed 2000 μm$^2$.liters/min to give the required deposition in the nasal cavity of the total dose. Resting ventilation is of the order of 30 liters/min.

Using the above types of delivery means, the required flow rate will be achieved by taking a rapid inhalation. Sufficient flow rate will not be achieved by merely normal resting ventilation.

Under extreme exertion or rapid inhalation, a very large fraction of the deposition takes place within the anterior non-ciliated part of the nose, where particles are retained for long periods, gradually being dragged along to the nasopharynx by the mucus drag effect. Details of deposition and flow rate studies may be found in the art, for example G. M. Hidy, Aerosols, Academic Press Inc. 1984.

For particulate systems administered to the respiratory tract, it is necessary to consider the aerodynamic diameter that takes into account the size of the particle and its density. For example, a particle with a physical diameter of 0.5 μm and density of 10 will behave like a larger particle (of greater than 2 microns) of unit density. This applies strictly to spherical particles and may be varied markedly by the shape of the particle. The aerodynamic (kinetic diameter) has been defined as the diameter of a hypothetical sphere of unit density having the same terminal settling velocity as a particle in question regardless of its geometric size, shape and true density.

The small microspheres of the present invention have been found to be easier to administer using available devices, especially those working on the basis of pressure packs and accurate valves and actuators, as fewer problems with blockages occur.

Small microspheres are also easier to fluidize in powder administration devices, such as insufflators.

The narrower size range has been found to give a more uniform dose for an active material such as a peptide. The narrower size range has also been found to minimize separation of large and small particles on storage and transport and during administration. The admixture of insulin and microcrystalline cellulose as described in the prior art such as EP 122 036 results in a system that can undergo separation of particles on storage, shipment and administration. For example, when evaluated using an Andersen Impactor, the insulin was found largely in the smaller size fractions and the cellulose in the larger fractions. This could lead to non-uniformity of dosing and unpredictive absorption. Greater control over the deposition site in the nose can be achieved with smaller and more uniform particles.

A BRIEF DESCRIPTION OF THE DRAWINGS

Preferred aspects of the invention will now be illustrated by way of example and with reference to the accompanying drawings, in which.

EXAMPLE 1

Comparative Biological Data (sheep)

Figure 1:
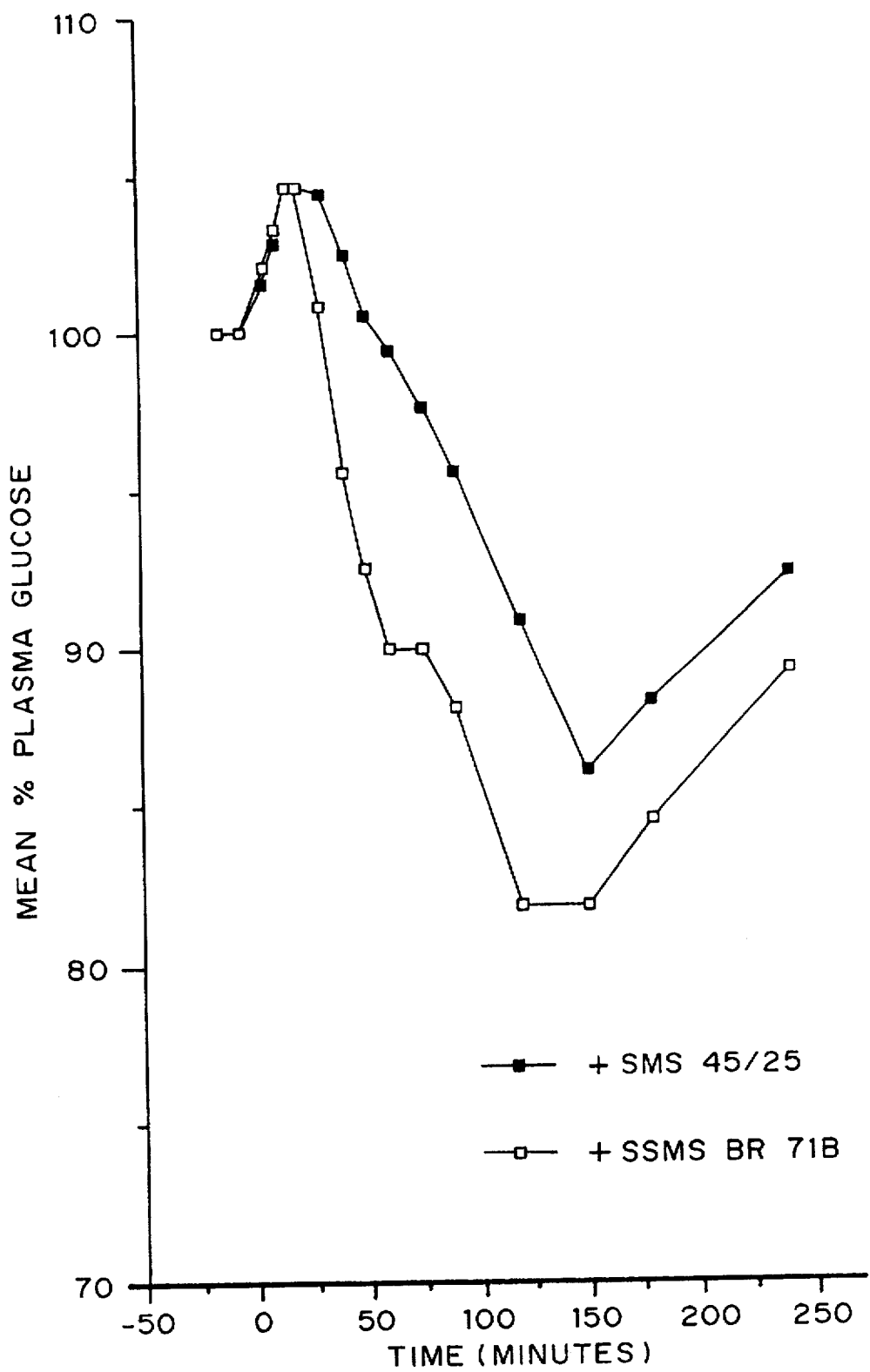
FIG. 1 shows the results of Example 1, illustrating intranasal administration of insulin at 2 IU/kg with 2 mg/kg of differently sized microspheres in sheep.
Figure 2:
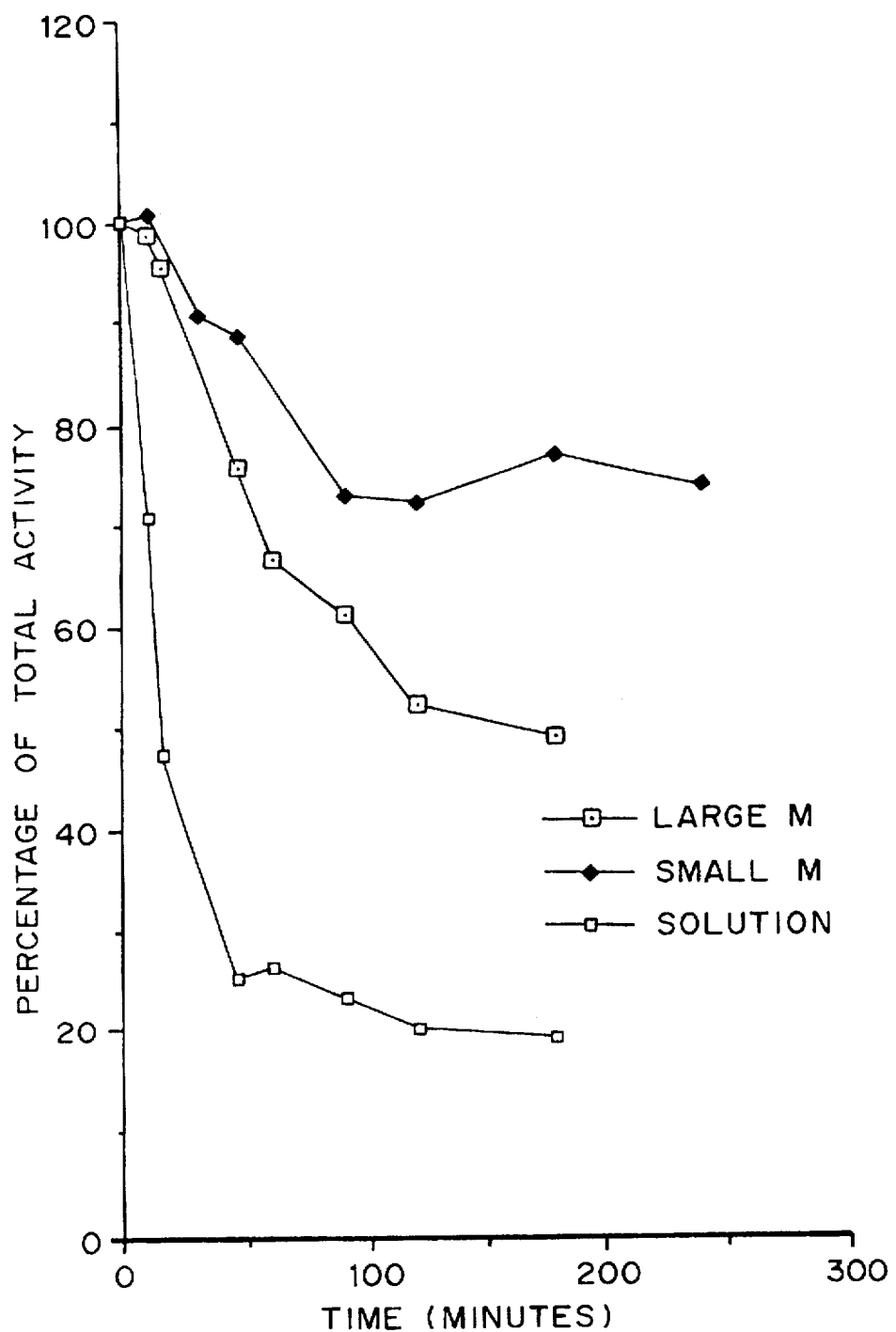
FIG. 2 shows the results of Example 2, illustrating the clearance of intranasally-administered, radiolabelled, large and small microsphere formulations and a liquid formulation, in humans.

Summary. Insulin was administered nasally to sheep at 2 IU/kg as a lyophilised powder with either starch microspheres 45/25 (SMS 45/25) or smaller (<10 microns) starch microspheres BR 71B 03C (SSMS BR 71B) at 2 mg/kg. After an initial small rise in both groups, the plasma glucose concentrations were generally lower after SSMS BR 71B co-administration. The lowest concentrations reached after SSMS BR 71B and SMS 45/25 co-administration were 82.0% and 86.2% of control at 150 minutes after dosing.

Materials and Methods

Semi-synthetic human Na-insulin (Nordisk, Gentofte, Batch No P389, 28 IU/mg) was used. The water content of the sample was determined by spectrophotometry, and the material was found to be 84.4% pure. Starch microspheres 45/25, Batch Number 49238) and smaller (<10 microns) starch microspheres BR 71B 03C (SSMS BR 71B, Batch Number 97327b), were supplied by Pharmacia.

Ultra pure water ("Elgastat UHP", Elga) was used throughout and all other reagents were at least of standard laboratory grade.

Sheep. Eight male cross-bred sheep weighing (±SEM) 29.0±1.07 kg were used. The sheep were normally housed indoors, and remained inside for the duration of the study. Animals were not fasted prior to insulin administration. An in-dwelling Viggo secalon cannula of 1.2 mm id, fitted with a secalon universal flow-switch, was placed approximately 15 cm into one of the external jugular veins of each animal on the first day of the study and, whenever necessary, kept patent by flushing it with heparinised (25 IU/ml) 0.9% saline solution. This cannula was removed upon the completion of the study and the sheep were returned to their normal housing.

Preparation of insulin formulations. For the preparation of these lyophilised microsphere formulations, a Solution of 50.8 mg insulin in 50 ml of water (1.016 mg/ml, 24 IU/ml) was prepared. The required quantity of each of the microspheres, SMS 45/25 or SSMS BR 71B (480 mg), was dispersed in 20 ml of insulin solution plus 12 ml of water (to keep the ratio of microspheres to solution at 15:1 [mg:ml]). The two resultant suspensions were stirred for one hour at room temperature and then freeze-dried to obtain the powder formulations (Formulations 1 and 2). The freeze-drying was performed on an Edwards Modulyo freeze-dryer fitted with a bell-jar assembly and operated at a pressure of 0.08 torr (10.7 $N/m^2$), a condenser temperature of −53° C. and a product shelf temperature of approximately 20° C. The freeze-drying process was allowed to proceed for 24 hours, after which the final product was loaded into the administration devices and then stored with dessicant at 4° C. for 16 hours prior to administration to the sheep.

Administration of insulin formulations and blood sampling. The sheep were divided into two groups of four animals each. Group 1: Four animals received 2.0 IU/kg insulin together with 2.0 mg/kg SMS 45/25 microspheres (Formulation 1) intranasally in the form of a lyophilised powder. A sheep of 30 kg thus received 60 IU of insulin together with 60 mg SMS 45/25 microspheres. Group 2: Four animals received 2.0 IU/kg insulin together with 2.0 mg/kg SSMS BR 71B microspheres (Formulation 2) intranasally in the form of a lyophilised powder. A sheep of 30 kg thus received 60 IU of insulin together with 60 mg SSMS BR 71B microspheres.

The sheep were sedated with an iv dose of ketamine hydrochloride (Ketalar®, 100 mg/ml injection) at 2.25 mg/kg and this anaesthesia lasted for about 3 minutes. This treatment acted as an animal restraint, and also as a countermeasure against the animal sneezing during administration. For intranasal administration a Leymed red rubber Magill's tube oral of 6.5 mm was loaded with the powder formulation and then inserted into the nostril of the sheep to a preset depth of 6 cm before blowing the powder into the nasal cavity. Blood samples of 6.0 ml were collected onto crushed ice from the cannulated jugular vein of the sheep at 15 and 5 minutes prior to the insulin administration and at 5, 10, 15, 20, 30, 40, 50, 60, 75, 90, 120, 150, 180 and 240 minutes post-administration. Each blood sample was divided into two parts. For insulin analysis, the blood collected (4.0 ml) was mixed gently in 4 ml heparinised tubes (Lithium Heparin, 60 IU, Sarstedt, Leicester, UK). For glucose analysis, the blood collected (2.0 ml) was mixed gently in 2 ml sodium fluoride tubes (2.0 mg fluoride and 30 IU heparin, Sarstedt, Leicester, UK). The plasma was separated by centrifugation at 4° C. and 3200 rpm, and then stored at –20° C. awaiting insulin and glucose analysis within our Analytical Section.

Analysis. Plasma glucose concentrations were analysed by the glucose oxidase method using a Yellow Springs 23 AM glucose analyser (Yellow Springs, Ohio, U.S.A.). Plasma insulin was not measured at this stage.

Results and discussion. The mean changes in plasma glucose following the co-administration of insulin with SMS 45/25 or SSMS BR 71B are plotted on the same axes in FIG. 1.

Both SMS 45/25 and SSMS BR 71B groups showed an initial rise in plasma glucose concentrations up to approximately 105.0% of the controls at approximately 20–30 minutes after dosing. Thereafter, concentrations of glucose steadily fell to a low point at approximately 150 minutes after dosing. At this low point the change in glucose concentration was greatest after co-administration of SSMS BR 71B (82.0%) than after co-administration of SMS 45/25 (86.2%). Indeed, after co-administration of SSMS BR 71B the glucose concentrations were generally lower than those after SMS 45/25 co-administration.

The area under the curve (AUC) is a particularly important measure of the effectiveness of the enhancer system: Group 1 gave a mean AUC of 1704% per minute, whereas Group 2 gave a mean AUC of 2766% per minute. This is a 62% increase in AUC, and was accompanied by a 25% increase in the blood concentration of insulin.

EXAMPLE 2

Comparative Biological Data (human)

Small starch microspheres were labelled with Tc99m using the stannous chloride technique and freeze dried. Doses of 30 mg were filled into hard gelatin capsules for the application. A group of healthy male and female volunteers (n=3) were each given the microsphere preparation using a Lomudal nasal insufflator. The total content of the capsules was applied during inhalation to the mucosal surface of either the right or the left nostril. The deposition and the subsequent clearance of the formulation were followed by gamma scintigraphy while the volunteers were positioned in an upright position with the nose in a fixed position dose to the collimator surface of the camera, using a specially designed template. Static views were recorded at times 0, 10, 30, 45, 90, 120, 180 and 240 min after administration. Regions of interest were drawn around the initial site of deposition and the total nasal cavity. The counts from each region were corrected for background counts and radioactive decay and expressed as a portion of the registered activity in the initial deposition site.

FIG. 2 shows a comparison between the clearance of small starch microspheres and large microspheres and a simple control solution. It can be seen that the half time of clearance for the small microspheres has not been reached within the time of the study, whereas the half time of clearance for the large microspheres is 180 min as compared to 15 min for the solution formulation.

Hence the use of the small microspheres (1–10 μm) as compared to the large microspheres (40 μm) gives a significantly longer residence time in the nasal cavity.

EXAMPLE 3

Investigation of the effect of different small hyaluronic acid microsphere formulations on the intranasal absorption of insulin by sheep The example investigates the effect of two different types of small (<10 μm) hyaluronic acid microspheres (HYAFF 11 and HYAFF 11 - dextran) on the nasal absorption of insulin. The results were compared with two control groups which were dosed either, nasally with insulin and large starch microspheres, or subcutaneously with insulin solution alone.

Materials and methods

Materials Semi-synthetic human Na-insulin (28 IU/mg) was used. The water content of the sample was determined by spectrophotometry at the time of use, and this purity was used for all subsequent calculations.

Hyaluronic acid microspheres HYAFF 11, ( <10 μm) prepared from the benzyl ester of hyaluronic acid (Batch number 102H11R), and HYAFF 11 - dextran (Batch Number 100H11RDex) (<10 μm) supplied by Fidia, were used.

Starch microspheres 45/25 (45 μm swollen/25 μm dry), (SMS, Batch Number 49238), from Pharmacia were used.

Ultra pure water ("Elgastat UHP", Elga) was used throughout.

All other reagents were, at least, of standard laboratory grade.

Sheep Sixteen sheep were used in this study.

The sheep were normally housed indoors, and remained inside for the duration of the study. The animals were not fasted prior to insulin administration. An in-dwelling cannula fitted with a flow-switch, was placed into one of the external jugular veins of each animal on the first day of the study and, whenever necessary, was kept patent by flushing it with heparinised saline solution. This cannula was removed upon the completion of the study, and the sheep were returned to their normal housing.

Preparation of insulin formulations For the preparation of the lyophilised microsphere formulations a solution of approximately 130 IU/ml (4.6 mg/ml) of pure insulin in water was prepared. The required quantity of each of the microspheres was dispersed in water and sonicated for 30 seconds. The appropriate volume of insulin solution was added to each microsphere suspension, and the volume adjusted with water to keep the ratio of microspheres to solution constant. The three resultant suspensions were stirred at room temperature, and then freeze-dried to obtain the powder formulations (Formulations 1 to 3). The freeze-drying process was allowed to proceed to completion, after which the final product were loaded into the administration devices and then stored, with dessicant, at 4° C. for 16 hours prior to administration to the sheep.

On the day of dosing the subcutaneous dosing solution (Formulation 4) was prepared comprising a solution of 10 IU/ml (0.357 mg/ml) of pure insulin in 0.9% saline.

Administration of insulin formulations The sheep were divided into four groups of four animals each and treated as shown in Table 1.

TABLE 1

| GROUP FORMULATIONS | Dose groups | | ACTUAL DOSES | | |
|---|---|---|---|---|---|
| | DOSES PER kg | | | | |
| | INSULIN (IU/mg) | MICROS. (mg) | SHEET | INSULIN (IU/mg) | MICROS (mg) |
| 1. HYAFF 11 | 2.0/0.071 | 2.0 | A | 72/2.571 | 72 |
| | | | B | 92/3.286 | 92 |
| | | | AF | 76/2.714 | 76 |
| | | | BF | 70/2.500 | 70 |
| 2. HYAFF 11 - dextran | 2.0/0.071 | 2.0 | C | 82/2.929 | 82 |
| | | | D | 82/2.929 | 82 |
| | | | CF | 70/2.500 | 70 |
| | | | DF | 74/2.643 | 74 |
| 3. SMS | 2.0/0.071 | 2.5 | E | 64/2.286 | 80 |
| | | | F | 78/2.786 | 97.5 |
| | | | EF | 74/2.643 | 92.5 |
| | | | FF | 58/2.071 | 72.5 |
| 4. S/C Insulin alone | 0.2/0.007 | — | G | 6.8/0.243 | — |
| | | | GF | 6.6/0.236 | — |
| | | | H | 6.8/0.243 | — |
| | | | HF | 8.8/0.314 | — |

For intranasal administration of the powder formulations (1 to 3) a tube was loaded with the formulation and then inserted into the nostril of the sheep to a preset depth, before blowing the powder into the nasal cavity. Subcutaneous injections were made into a shaved site at the neck, using a suitable syringe. The dose volume was 0.02 ml/kg.

Sedation/Blood Sampling The sheep were sedated using an intravenous dose of ketamine hydrochloride. This was intended for animal restraint, and also as a counter-measure against the animal sneezing during administration. (Sheep D did sneeze soon after administration). The anaesthesia lasted for about 3 minutes. Blood samples of 4.0 ml were collected onto crushed ice from the cannulated jugular vein of the sheep at 15 and 5 minutes prior to the insulin administration and at 5, 10, 15, 20, 30, 40, 50, 60, 75, 90, 120, 150, 180 and 240 minutes post-administration. Blood samples were mixed gently in 4 ml heparinised tubes. The plasma was separated by centrifugation and each plasma sample was divided into two aliquots of approximately 1 ml. The plasma was then stored at −20° C. awaiting analysis by our Analytical Section.

Glucose analysis Plasma glucose concentrations were measured using a Yellow Springs YSI 23 AM blood glucose analyser (Yellow Springs. Ohio, U.S.A.).

Calculation of results The plasma glucose concentrations were determined as mmol/l. The two control plasma glucose concentrations (−15 and −5 minutes) for each animal were meaned and all test plasma concentrations were expressed as a percentage of these mean control values. Results are therefore percent of control plasma concentrations.

The area between 100% and the actual blood glucose curve (area of fall from control) was calculated using the trapezoidal method.

Figure 3:
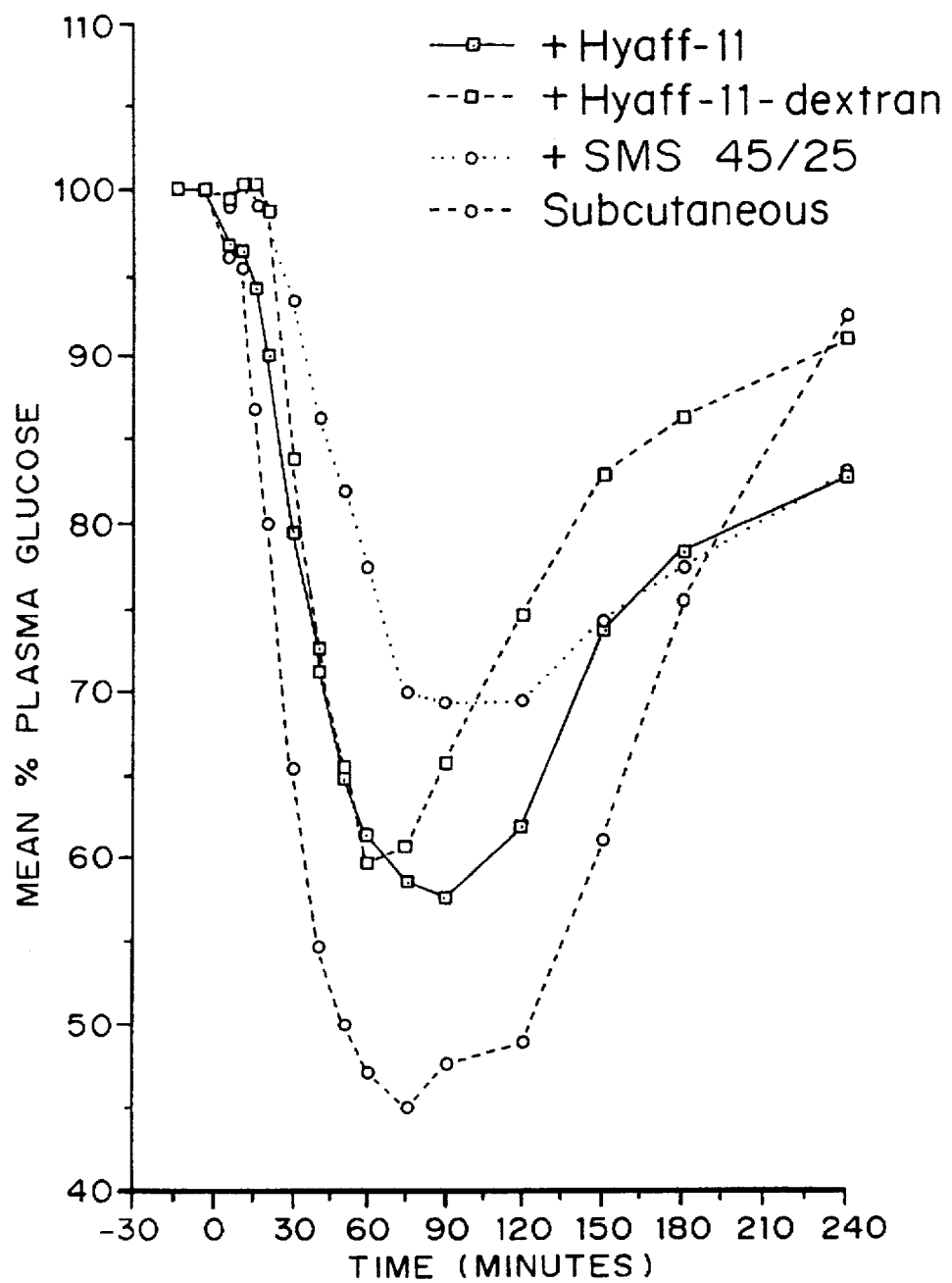
FIG. 3 shows the results of Example 3 illustrating the effect of intranasal administration of insulin with small (<10 μm) hyaluronic acid microspheres compared with large starch microspheres in sheep.

Results and discussion The mean (+SEM) values for the percent of control plasma glucose concentration following administration of insulin nasally with Hyaff 11, Hyaff 11 - dextran or SMS, together with administration via the subcutaneous route, are shown in FIG. 3. These results illustrate that all formulations caused a marked decline in plasma glucose concentrations. However, from the results shown in FIG. 3, it can be seen that the decrease in plasma glucose level was significantly faster and greater with both of the small (<10 μm) hyaluronic acid microsphere formulations than with the large starch microsphere formulation.

I claim:

1. A method for systemically delivering an active drug to a mammal, the method comprising:

a) providing a composition comprising a plurality of bioadhesive microspheres comprising a material selected from the group consisting of polysaccharides, proteins, and synthetic polymers, wherein the polysaccharide is selected from the group consisting of a starch, a dextran, a hyaluronic acid, a gellan gum and pectin and the protein is selected from the group consisting of gelatin, albumin, and collagen, and an active drug selected from the group consisting of proteins and peptides, and non-protein drugs selected from the group consisting of antibiotics, anesthetics, vasoconstrictors, cardiotonics, vasodilators, antiseptics, bone metabolism controlling agents, hypotensives, sedatives, anti-tumour agents, anti-inflammatory agents, anti-histaminic agents, anti-allergic agents, and antitussive-expectorant agents, wherein at least 90 wt % of the microspheres in the composition have a diameter between 0.1 μm and 10 μm; and b) administering the composition to a mammal intranasally thereby to systemically delivery a therapeutically effective amount of the drug to the mammal.

2. The method of claim 1 for delivering a drug to the nasal mucosa, comprising introducing a gas stream containing the composition into the nose.

3. The method of claim 1 for treating diabetes comprising introducing a gas stream containing the composition into the nose, wherein the systemically active drug is insulin.

4. The method of claim 1 wherein the bioadhesive material is selected from the group consisting of gelatin, albumin and collagen.

5. The method of claim 4 wherein the microspheres comprise starch.

6. The method of claim 1 wherein the microsphere material is cross-linked prior to step b).

7. The method of claim 1 wherein the microspheres are treated by heating prior to step b).

8. The method of claim 1 the composition provided in step a) further comprises an absorption enhancer.

9. The method of claim 8 wherein the absorption enhancer is a surfactant.

10. The method of claim 1 wherein the drug is a biologically active peptide.

11. The method of claim 10 wherein the peptide is insulin or calcitonin.

12. The method of claim 1 wherein the bioadhesive material is selected from the group consisting of polyvinyl alcohol, polylactide-co-glycolide, hyaluronic acid, gellan gum and pectin.

13. The method of claim 1 wherein the bioadhesive material is selected from the group consisting of hydroxyethyl starch, hydroxypropyl starch, carboxymethyl starch, cationic starch, acetylated starch, phosphorylated starch and grafted starch.

* * * * *

(12) EX PARTE REEXAMINATION CERTIFICATE (5691st)
United States Patent
Illum

(10) Number: US 5,707,644 C1
(45) Certificate Issued: Mar. 6, 2007

(54) SMALL PARTICLE COMPOSITIONS FOR INTRANASAL DRUG DELIVERY

(75) Inventor: Lisbeth Illum, The Park (GB)

(73) Assignee: West Pharmaceutical Services Drug Delivery & Clinical Research Centre Limited, Nottingham (GB)

Reexamination Request:
No. 90/007,567, Jun. 2, 2005

Reexamination Certificate for:
Patent No.: 5,707,644
Issued: Jan. 13, 1998
Appl. No.: 08/359,937
Filed: Dec. 20, 1994

Related U.S. Application Data

(63) Continuation of application No. 08/065,676, filed on May 21, 1993, now abandoned, which is a continuation-in-part of application No. 07/842,351, filed on Mar. 24, 1992, now abandoned, and a continuation-in-part of application No. PCT/GB90/01676, filed on Nov. 1, 1990.

(30) Foreign Application Priority Data

Nov. 4, 1989 (GB) ............................................. 8924935

(51) Int. Cl.
*A61K 9/16* (2006.01)
*A61K 9/00* (2006.01)
*A61K 9/51* (2006.01)
*A61K 47/24* (2006.01)

(52) U.S. Cl. ........................ 424/434; 424/489; 424/499; 424/500; 424/501; 424/866

(58) Field of Classification Search ........................ None
See application file for complete search history.

(56) References Cited

U.S. PATENT DOCUMENTS

| 4,250,163 | A | * | 2/1981 | Nagai et al. ............. 514/772.1 |
| 4,294,829 | A | * | 10/1981 | Suzuki et al. ............... 514/174 |
| 4,462,983 | A | * | 7/1984 | Azria et al. .................... 424/45 |
| 4,851,521 | A | * | 7/1989 | della Valle et al. ........ 536/55.1 |

FOREIGN PATENT DOCUMENTS

| EP | 023359 A2 | * | 2/1981 |
| EP | 122036 A1 | * | 10/1984 |
| EP | 178433 A1 | * | 4/1986 |
| GB | 1520247 | * | 8/1978 |
| GB | 1520248 | * | 8/1978 |
| WO | WO 87/03197 | * | 6/1987 |

OTHER PUBLICATIONS

Morimoto et al. J. Pharm. Pharmacol. 1985, 37:134–136.*
Fisher et al. J. Pharm. Pharmacol. 1985, 37:38–41.*
Illum L. Nato ASI Symposium. 1986, pp. 205–210.*

* cited by examiner

*Primary Examiner*—Evelyn Mei Huang

(57) ABSTRACT

A drug delivery composition for intranasal delivery comprises a plurality of bioadhesive microspheres and active drug associated with each microsphere, at least 90 wt % of the microspheres having a diameter in the range 0.1 µm to 10 µm. The microspheres may be of starch, gelatin, dextran, collagen or albumin. Suitable drugs include peptides, such as insulin, and antigenic vaccine ingredients. The composition may additionally comprise an absorption enhancer. The microspheres are administered m the nasal cavity by a means such that the product of the square of the microsphere diameter and the flow rate is greater than 2000 µm².liters/min.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–13 are cancelled.

* * * * *